United States Patent [19]

Opolski

[11] Patent Number: 5,272,012

[45] Date of Patent: Dec. 21, 1993

[54] MEDICAL APPARATUS HAVING PROTECTIVE, LUBRICIOUS COATING

[75] Inventor: Margaret P. Opolski, Fort Polk, La.

[73] Assignee: C. R. Bard, Inc., Murray Hill, N.J.

[21] Appl. No.: 827,362

[22] Filed: Jan. 29, 1992

Related U.S. Application Data

[63] Continuation-in-part of Ser. No. 720,918, Jun. 25, 1991, abandoned, which is a continuation of Ser. No. 370,917, Jun. 23, 1989, Pat. No. 5,026,607.

[51] Int. Cl.$^5$ .................. B32B 27/00; B32B 27/40
[52] U.S. Cl. .................. 428/423.1; 427/2; 428/447; 428/423.7; 604/96; 604/265; 606/194
[58] Field of Search .............. 427/2; 428/423.1, 423.7, 428/447; 604/96, 265; 606/194

[56] References Cited

U.S. PATENT DOCUMENTS

| | | | |
|---|---|---|---|
| 4,011,189 | 3/1977 | Keil | 252/12 X |
| 4,263,188 | 4/1981 | Hampton et al. | 427/128 X |
| 4,301,053 | 11/1981 | Wolfrey | 428/412 X |
| 4,306,998 | 12/1981 | Wenzel et al. | 528/48 X |
| 4,598,120 | 7/1986 | Thomas et al. | 524/591 |
| 4,605,698 | 8/1986 | Briden | 524/559 |
| 4,642,267 | 2/1987 | Creasy et al. | 428/413 |
| 4,666,437 | 5/1987 | Lambert | 427/2 X |
| 4,675,361 | 6/1987 | Ward, Jr. | 525/92 |
| 4,739,013 | 4/1988 | Pinchuk | 264/331.19 X |
| 4,769,030 | 9/1988 | Pinchuk | 427/2 X |
| 4,851,009 | 7/1989 | Pinchuk | 427/2 X |
| 5,019,096 | 5/1991 | Fox, Jr. et al. | 623/1 |
| 5,034,461 | 7/1991 | Lai et al. | 525/100 |

Primary Examiner—Michael Lusignan
Attorney, Agent, or Firm—Wolf, Greenfield & Sacks

[57] ABSTRACT

A method for providing a medical apparatus with a protective, lubricious coating is described. The method comprises providing a coating solution which contains a protective compound such as a urethane, a slip additive such as a siloxane, and optionally, a crosslinking agent for the protective compound such as a polyfunctional aziridine, coating the solution onto a surface of a medical apparatus and allowing the coating to set. The resulting surface coating is lubricious, tough and flexible. The coating is well suited for use with materials used as components of balloon catheters.

73 Claims, No Drawings

MEDICAL APPARATUS HAVING PROTECTIVE, LUBRICIOUS COATING

Related Applications

This is a continuation-in part of serial, no. 07/720,918, filed on Jun. 25, 1991, now abandoned, which is a continuation of serial number 07/370,917 filed on Jun. 23, 1989, now U.S. Pat. No. 5,026,607 issued Jun. 25, 1991, both entitled Medical Apparatus Having Protective, Lubricious Coating. The contents of both parent applications are hereby expressly incorporated by reference.

BACKGROUND OF THE INVENTION

In coronary angioplasty and related technologies, a catheter having an inflatable balloon attached at the catheter's distal end is employed. Such balloons have been known to fail by damage resulting from abrasion and puncture during handling and use and also from over-inflation. Additionally, the balloons and catheters upon which they are mounted generally have a higher coefficient of friction than desired for ease of use. Thus, it often becomes difficult to guide the catheter into a desired location in a patient due to friction between the apparatus and the vessel through which the apparatus passes.

A variety of urethane based coating compositions for medical applications are known in the art. For example, U.S. Pat. 4,642,267 to Creasy et al. describes hydrophilic polymer blends useful for coating catheters and other surfaces. The coating comprises a thermoplastic polyurethane and a hydrophilic poly (N vinyl lactam) such as polyvinylpyrrolidone. Additional components such as crosslinking agents and wax dispersions can be added to the blend. U.S. Pat. No. 4,675,361 to Ward, Jr. relates to polymer systems useful for coating surfaces having blood and tissue contacting applications.

Although each of these patents describes an application involving biomedical apparatus, a need still exists for a simple, easy to apply coating which is biocompatible, lubricious and provides a protective layer to the surface upon which it is applied.

SUMMARY OF THE INVENTION

The present invention pertains to methods for providing protective, lubricious coatings on surfaces of medical apparatus. The coatings contain a protective compound for protecting the surface of the medical apparatus and a slip additive for enhancing the lubricity of the surface of the medical apparatus. The protective compound binds the slip additive such that domains of the slip additive are exposed in the formed layer. The coating solution also may contain a crosslinking agent.

The method of this invention also may provide a formed coating layer containing the protective compound being crosslinked to itself and to functional moieties derived from the medical apparatus. This type of crosslinking strengthens the overall layer and enhances the adhesion of the coating to the medical apparatus.

The present invention also pertains to medical apparatus coated with the above described protective, lubricious surface coatings. The medical apparatus may comprise a balloon, catheter or guidewire.

DETAILED DESCRIPTION OF THE INVENTION

As used herein, the term "medical apparatus" means apparatus suited for use in medical applications, particularly in in vivo applications. Such apparatus specifically includes, but is not limited to, balloons, catheters, guidewires, stylets and introducers. Of particular note for use with the invention are catheters having inflatable balloons such as those developed for use in angioplasty and valvuloplasty, guide catheters and guidewires.

As used herein, the term "protective compound" means a substance capable of protecting the surface of a medical apparatus upon which it is coated. The protective compound preferably provides a network for containing a slip additive such that domains of the slip additive are exposed in the formed coating layer. The protective compound preferably has functional moieties capable of crosslinking to other moieties within the protective compound and with moieties derived from the medical apparatus. This type of crosslinking enhances the strength, adhesion, and toughness of the coating.

The language "moieties derived from the medical apparatus" is intended to include functional moieties from the material of which the medical apparatus is made, moieties from a primer layer disposed between the protective, lubricious coating and the medical apparatus or moieties generated or formed by subjecting the material of which the medical apparatus is made or the primer layer to a pretreatment step, e.g., plasma or corona discharge. Examples of protective compounds include resin systems such as urethanes, acrylics, vinylidene chlorides and vinyls. Water based urethanes are particularly desirable due to their protective qualities and their ability to provide a carboxyl functionality allowing crosslinking within the urethane itself and binding with carboxyl groups present on the surface of the medical apparatus.

As used herein, the term "slip additive" means a substance capable of imparting a lower coefficient of friction to the surface of a medical apparatus. Preferably, the slip additive is capable of being included in a protective network. The slip additives of the present invention may be hydrophobic or hydrophilic. The slip additive also may be crosslinkable to the functional moieties from the protective compound and/or functional moieties derived from the medical apparatus. The slip additive also may have a moiety or moieties that prolong the time period for which the slip additive remains in the network, i.e., allows it not to wear out for a prolonged period of time. Examples of slip additives include silicon based compounds such as silicones and siloxanes, fluorochemicals such as polytetrafluoroethylene (PTFE), polyvinylpyrrolidone copolymers, similar polymers and copolymers, e.g., other lactams, and a variety of waxes.

As used herein, the term "crosslinking agent" is intended to include agents capable of enhancing the crosslinking of the protective compound or the slip additive. The crosslinking agent further may enhance the adhesion of the coating to the medical apparatus. For example, functional moieties of the protective compound may be crosslinked to other functional moieties derived from the medical apparatus. Also, the slip additive may contain functional moieties capable of crosslinking with moieties from the protective compound and/or moieties derived from the medical apparatus. The functional moieties are intended to include groups capable of binding to one another. The protective compound and slip additive may be selected because of such functional moieties. Examples of crosslinking agents useful within this invention are aziridine, carbodiimides, urea, melamine formaldehyde condensates, epoxys, and isocyanates. One skilled in the art would know that the crosslinking agent is selected based upon the functional moieties desired to be crosslinked and substrate temperature limitations.

As used herein, the term "primer layer" is intended to include a layer capable of providing the desired adhesion to substrate and functional moieties for crosslinking to the protective compound and/or slip additive. The primer layer is disposed between the medical apparatus and the protective, lubricious coating layer. A material which is useful and desirable for making medical apparatus may not possess functional moieties capable of crosslinking sufficiently with a desired protective compound and/or slip additive. In this situation, the desired functional moieties can be provided to the surface of the medical apparatus by coating the apparatus with a primer layer. An example of such a layer is a dispersion of ethylene acrylic acid (EAA) which is capable of providing carboxyl moieties to the surface.

As an alternative to the use of a primer, a surface functionality can be obtained on the substrate surface using a variety of other techniques. For example, surface functionality can be obtained using a plasma or corona discharge or by exposing the surface to a flame. In the case of plasma or corona discharge, the functionality obtained on the surface can be tailored through the use of process atmosphere variation. Thus, when an oxygen derived functionality (i.e. —OH or —COOH) is desired, the surface can be plasma treated in an oxygen-containing atmosphere. Alternatively, if an amine functionality is preferred, the treating process can be carried out in a nitrogen containing atmosphere.

As used herein, the term "coating solution" is intended to include a solution containing both the protective compound and the slip additive capable of being coated on a surface of a medical apparatus. The coating solution has a solids content by weight (hereinafter solids content) sufficient to allow the solution to be applied to the medical apparatus. The solution preferably has between about 2% to about 80% solids content, more preferably 10% to about 50% solids content, and most preferably about 15% to about 25% solids content. The solution further preferably is an aqueous solution.

The coating solution also may include other materials which do not detrimentally effect the protective compound and slip additive network. These materials include pigments, radioopaque compounds, therapeutic agents, and antimicrobial agents. The term therapeutic agent for purposes of this invention is intended to include substances capable of providing a therapeutic effect in the environment of use of the medical apparatus. The therapeutic agents may be anti inflammatory agents, antibiotics, immunesuppressible stimulatory agents, anti thrombolytic agents, growth factors, agents that locally effect blood pressure, and agents that promote cell survival and healing. One of ordinary skill in the art would know and select agents capable of attaining a desired function or result. Antimicrobial agents are agents capable of suppressing the growth or activity of microorganism allowing them to combat infections. Examples of classes of antimicrobial agents include antibiotics, iodine solutions, mercurials nitroimidazoles, bisguanidessilier or phenolics. Specific examples of agents within classes include metronidazole and chlorhexidine. The therapeutic or antimicrobial agents may be released from the coating in vivo, e.q., sustained release, or may not be released if it possesses activity while being maintained in the coating.

The material can be applied to surfaces using any of a variety of methods. Preferred among these are dipping, spray coating, rolling and brushing. Subsequent to the actual coating step, the coated devices are allowed to cure. The curing may be carried out by placing the coated devices in an oven, e.g. at approximately 50° C. for urethane, until the protective compound is fully dried. Alternatively, the coating may be air dried. The temperature selected for the curing step may depend on the temperature limitations of the substrate and reactivity of crosslin Ker.

The resulting coating is flexible, durable and lubricious, retaining its lubricity for an extended period of time. These properties are a direct result of the protective compound's ability to act as a binder to maintain domains of the slip additive. Thus the durable binder enhances lubricity by preventing the removal of the slip additive from the substrate surface. Additionally, the protective compound provides an abrasion resistance to the substrate surface, thereby minimizing the effect of abuse on the device.

In the case of PET balloons, the abrasion resistance provided by the coating is particularly desirable since it substantially reduces damage to the balloon surface. This decreases the likelihood of balloon failure caused by mishandling during balloon preparation or use.

In the case of most water based coatings, e.g., urethane based, bonding of the coating to the substrate surface upon which it is applied can be achieved by a crosslinking reaction between carboxyl functional groups present in the coating, e.g., urethane, and carboxyl functional groups present on the substrate surface. One method by which such bonding can be achieved involves a crosslinking reaction utilizing the aforementioned polyfunctional aziridine through which the linkage will occur.

In a preferred embodiment, the coating is provided in the form of a solution having a solids content of between about 15% and about 25% and which comprises a water based urethane dispersion, a dimethyl siloxane emulsion containing at least about 15% solids and a polyfunctional aziridine. Unless otherwise noted, all percentages described herein are percentaqes by weight. Other materials, such as pigments, radioopaque compounds, antimicrobial agents and therapeutic agents can be added as well.

A high molecular weight, hard, non yellowing, water based urethane is preferred as the resin of the coating. Particularly preferred is a urethane dispersion having a solids content of between about 30% and about 50% in a solution comprising a mixture of water, N Methyl 2 pyrrolidone (CAS# 872 50 4) and triethylamine (CAS# 121-44-8). Such a dispersion is available from Permuthane (Peabody, MA) as UE41 222. It is particularly desirable that the protective compound be dispersed in a liquid which will not harm the surface upon which the coating is applied. Thus, for a surface such as a PET balloon, the urethane is preferably provided as a dispersion in an aqueous medium.

The slip additive is preferably an emulsion of an industrial grade dimethyl siloxane in water having a siloxane content of at least about 15%. While a slip additive having up to about 100% siloxane or silicone can be used, an aqueous emulsion of the material diluted to about 15% solids is easier to handle during mixing of the coating solution. A preferred dimethyl siloxane is available from Dow Corning Corporation (Midland, MI) as Q2-3238. This is available neat and can be subsequently combined with water to form an emulsion having approximately 15% dimethyl siloxane.

When used in a urethane based coating, the crosslinking agent is preferably a polyfunctional aziridine. Although this material can be diluted prior to use, it is preferably used neat to minimize further dilution of the coating solution. Most preferred is the material available from Permuthane (Peabody, MA) as KM10 1703. This material will hydrolyze in water or humid air and reacts rapidly with acids. Once added to the coating solution, application should be within about 48 hours if room temperature conditions are maintained. Increased temperature will cause increased hydrolysis, inactivity of the material and promotion of crosslinking of the coating, resulting in a higher coating viscosity. Since the aziridine component is caustic, it must be fully reacted or hydrolyzed before the coated medical apparatus is suitable for in vivo use.

A most preferred coating formulation has a solids content of 17% upon application and comprises a mixture containing 42.55% UE41 222 urethane dispersion, 12.77% Q2-3238 siloxane dispersion, 2.13% KM10-1703 polyfunctional aziridine and 42.55% distilled water. The formulation can be made by mixing the siloxane emulsion with the distilled water and subsequently adding the urethane dispersion. This is then mixed in a capped glass container with a magnetic stirrer until all parts are thoroughly mixed. The crosslinking agent is subsequently added to the solution just prior to application of the coating upon a surface. The addition of the crosslinking agent just prior to application of the coating prevents the urethane from crosslinking only with itself and thereby allows a sufficient carboxyl group density within the coating for crosslinking with the surface to be coated.

In a most preferred application, the coating solution is intended to be used to provide a flexible, protective and lubricious coating to the surface of angioplasty balloons. These balloons can be made of a variety of materials such as polyvinyl chloride and polyethylene, although polyethylene terephthalate (PET) is preferred. Unfortunately, PET lacks the requisite density of available carboxyl groups to provide for satisfactory bonding of the urethane based coating with the surface. Therefore, it is often desirable to provide a first layer of a primer material between the PET balloon surface and the coating.

A preferred primer is a dispersion containing an ethylene acrylic acid (EAA) resin. A preferred EAA resin such as Primacor 5980 available from Dow Corning Corporation (Midland, MI) can be mixed in an aqueous solution to provide a formulation containing approximately 25% solids. As with the topcoat formulation, the EAA resin must be applied from a solvent which will not damage the surface of the apparatus to be coated. When applying the primer to a PET balloon, the EAA should be dissolved in an aqueous solvent. Since EAA resin has a very low solubility in water, it is necessary to first convert the EAA into a soluble salt. This can be accomplished by combining the resin with a quantity of ammonia sufficient to neutralize the carboxyl groups contained therein.

The required amount of ammonia is added to a volume of water into which a sufficient quantity of EAA has been mixed to form a dispersion. The container into which the components have been poured is then sealed and heated to approximately 110° C. for between about 15 and 30 minutes. The solution is then allowed to cool at which point it is ready for use. It should be noted that during the mixing steps, it is desirable to use a condenser to prevent evaporation of any of the components prior to sealing the mixing vessel.

As with the topcoat solution, the primer can be applied to the substrate surface using a wide variety of methods including, but not limited to, dipping, spray coating, rolling and brushing. Once applied, the primer should be cured until completely dry. Heat curing at approximately 50° C. has been found to be satisfactory for the EAA primer described previously. Subsequently, the topcoat solution can be applied to the primer coated device surface using the method previously described.

When the surface to be coated comprises a catheter mounted balloon, it is preferred that the balloon be inflated prior to applying the primer and/or topcoat. This allows the formation of a coating layer having a generally uniform thickness and also prevents adhesion between balloon surfaces that may contact one another in the deflated state. Care should be taken to ensure that no primer or topcoat is allowed to remain within any open lumen of the catheter as this will likely cause undesirable lumen blockages. Blotting the catheter end and any exposed lumen ports with a suitable blotting material subsequent to applying the layer will prevent such blockages. Alternatively, the catheter lumens can be purged using air or an inert gas.

Since the preferred topcoat solution contains both a slip additive and a crosslinker for the protective compound, the solution can be applied to surfaces having adequate functional group density in a single pass. This provides a process efficiency, as it eliminates the need to carry out a crosslinking step subsequent to application of the coating to the substrate surface.

When applied to the surface of PET balloons, the coating described herein has resulted in enhanced scratch resistance and a decreased coefficient of friction without noticeably altering the balloon profile or flexibility.

The present invention will be further illustrated by the following non limiting examples:

EXAMPLE 1

A coating solution was prepared in accordance with the teachings of this invention having the following formulation:

| Component | Supplier/Designation | Weight % |
|---|---|---|
| Urethane | Permuthane/UE41-222 | 42.55 |
| Dimethyl Siloxane Emulsion | Dow/Q2-3238 (15% in $H_2O$) | 12.77 |
| Aziridine | Permuthane/KM10-1703 | 2.13 |
| Distilled water | — | 42.55 |

The coating solution was prepared by first forming an emulsion of the dimethyl siloxane and distilled water having a siloxane content of about 15% by weight. The siloxane emulsion (12.77 q) was mixed with the distilled water (42.55 q). A urethane dispersion (Permuthane/UE41 222) was obtained from Permuthane (Peabody, MA). The urethane dispersion (42.55 q) was added to the water/siloxane mixture. The urethane/siloxane/water mixture was stirred in a capped glass container with a magnetic stirrer until all parts were thoroughly mixed. The aziridine (2.13 g) was added to the mixture just prior to the application of the coating onto a balloon catheter.

The coating solution was applied to a balloon catheter having a 3.0×20 mm PET balloon bonded to the catheter with a UV-activated adhesive, by dipping the inflated catheter into a volume of the coating mixture. Subsequent to the dipping, the coated apparatus was heat cured at approximately 50° C. until dry and then sterilized using ethylene oxide. Testing of the catheter was carried out using an uncoated balloon catheter as a control.

The two catheters were individually passed through an 8F (0.072") channel having a curvature replicating that of the final curve of an FL4 guide catheter. A 0.14" PTFE coated guidewire was used. The force of pushing and pulling the catheter was measured for different insertion lengths and the average minimum and maximum forces (in grams) for 10 cycles of both pushing and pulling of the coated and uncoated catheters were determined. The results of this test are summarized below:

| Sample | Push, g (min.) | Push, g (max.) | Pull, g (min.) | Pull, g (max.) |
|---|---|---|---|---|
| Coated | 11.0 | 32.5 | 8.4 | 25.4 |
| Uncoated | 20.5 | 42.5 | 16.7 | 33.0 |
| % Improvement Coated v. Uncoated | 46% | 21% | 50% | 23% |

As evidenced by the above, the coated catheter displayed a lower resistance to both pushing and pulling through the channel. This reduced resistance represented an average improvement of approximately 34% overall when comparing the coated catheter to the uncoated control catheter.

EXAMPLE 2

A coating solution is prepared in accordance with the teachings of this invention having the following formulation:

| Component | Supplier/Designation | Weight (%) |
|---|---|---|
| Acrylic | ICI Resins (A602 at 20% solids) | 68.30 |
| Dimethyl Siloxane Emulsion | Dow/Q2-328 (18% in H$_2$O) | 29.30 |
| Aziridine | Permuthane/KM10-1703 | 2.40 |

The coating solution is prepared by first forming an emulsion of the dimethyl siloxane and distilled water having a siloxane content of 18% by weight. An acrylic resin is obtained from ICI Resins (Wilmington, MA). The siloxane emulsion (29.30 g) is mixed with the acrylic resin (68.30 g). The acrylic/siloxane mixture is stirred in a capped glass container with a magnetic stirrer until all parts are thoroughly mixed. The aziridine (2.40 q) is added to the mixture just prior to the application of the coating onto a balloon catheter.

The coating solution is applied to a balloon catheter having a 3.0×20 mm PET balloon by dipping the inflated catheter into a volume of the coating mixture. Subsequent to the dipping, the coated apparatus is heat cured at approximately 50° C. until dry and then sterilized using ethylene oxide.

EXAMPLE 3

A coating solution is prepared in accordance with the teachings of this invention having the following formulation:

| Component | Supplier/Designation | Weight (%) |
|---|---|---|
| Urethane | Permuthane/UE41-222 (at 20% solids) | 68.30 |
| Wax | Chemcor/AC392N35 | 19.50 |
| Aziridine | Permuthane/KM10-1703 | 2.40 |
| Distilled water | — | 9.80 |

The coating solution is prepared by first mixing the wax (19.50g) with the distilled water (9.80g). A urethane dispersion (Permuthane/UE41-222) is obtained from Permuthane (Peabody, MA). The urethane dispersion (68.30 g) is added to the water/wax mixture. The urethane/wax/water mixture is stirred in a capped glass container with a magnetic stirrer until all parts are thoroughly mixed. The aziridine (2.40 g) is added to the mixture just prior to the application of the coating onto a balloon catheter.

The coating solution is applied to a balloon catheter having a 3.0×20 mm PET balloon by dipping the inflated catheter into a volume of the coating mixture. Subsequent to the dipping, the coated apparatus is heat cured at approximately 50° C. until dry and then sterilized using ethylene oxide.

EXAMPLE 4

A coating solution is prepared in accordance with the teachings o this invention having the following formulation:

| Component | Supplier/Designation | Weight (%) |
|---|---|---|
| Urethane | Permuthane/UE41-222 (at 20% solids) | 60.60 |
| Dimethyl siloxane | Dow/Q2-3238 (18% in H$_2$O) | 18.60 |
| Carbodiimide | Union Carbide/XL-25SE | 7.00 |
| Distilled water | — | 13.80 |

The coating solution is prepared by first forming an emulsion of the dimethyl siloxane and distilled water having a siloxane content of about 18% by weight. The siloxane emulsion (18.60 g) is mixed with the distilled water (13.80 q). A urethane dispersion (Permuthane/UE41 222) is obtained from Permuthane (Peabody, MA). The urethane dispersion (60.60 q) is added to the water/siloxane mixture. The urethane/siloxane/water mixture is stirred in a capped glass container with a magnetic stirrer until all parts were thoroughly mixed. The carbodiimide (7.00 g) is added to the mixture just prior to the application of the coating onto a balloon catheter.

The coating solution is applied to a balloon catheter having a 3.0×20 mm PET balloon by dipping the inflated catheter into a volume of the coating mixture. Subsequent to the dipping, the coated apparatus is heat cured at approximately 50° C. until dry and then sterilized using ethylene oxide.

EXAMPLE 5

A coating solution is prepared having the following formulation:

| Component | Supplier/Designation | Weight (%) |
|---|---|---|
| Urethane | Permuthane/UE41-222 (at 20% solids) | 66.70 |
| Polyvinylpyrrolidone copolymer | GAF/ACP 1030 (postneutralized) | 13.30 |
| Aziridine | Permuthane/KM10-1703 | 4.80 |
| Distilled water | — | 15.20 |

The coating solution is prepared by first mixing the polyvinylpyrrolidone (PVP-13.30q) with the distilled water (15.20 g). A urethane dispersion (Permuthane/UE41 222) is obtained from Permuthane (Peabody, MA). The urethane dispersion (66.70 q) is added to the water/siloxane mixture. The urethane/PVP/water mixture is stirred in a capped glass container with a magnetic stirrer until all parts were thoroughly mixed. The aziridine (4.80 g) is added to the mixture just prior to the application of the coating onto a balloon catheter.

The coating solution is applied to a balloon catheter having a 3.0×20 mm PET balloon by dipping the inflated catheter into a volume of the coating mixture. Subsequent to the dipping, the coated apparatus is heat cured at approximately 50° C. until dry and then sterilized using ethylene oxide.

EQUIVALENTS

Those skilled in the art will be able to ascertain, using no more than routine experimentation, many equivalents of the specific embodiments of the invention described herein.

These and all other equivalents are intended to be encompassed by the following claims.

What is claimed is:

1. A method for providing a protective, lubricious coating on a surface of a medical apparatus, the method comprising:
   applying a coating solution to a surface of the medical apparatus such that a protective, lubricious layer is formed upon the apparatus surface,
   wherein the coating solution comprises a protective compound and a slip additive and the formed layer contains the protective compound as a binder to maintain domains of the slip additive such that lubricating amounts of the slip additive are exposed to provide lubricity.

2. A method as claimed in claim 1 wherein the coating solution in the applying step further comprises a crosslinking agent for the protective compound.

3. A method as claimed in claim 2 wherein the crosslinking agent enhances the adhesion of the coating to the medical apparatus.

4. A method as claimed in claim 2 wherein the crosslinking agent is aziridine.

5. A method as claimed in claim 2 wherein the crosslinking agent is a carbodiimide.

6. A method as claimed in claim 1 wherein in the applying step, the protective compound in the formed layer is crosslinked.

7. A method as claimed in claim 6 wherein the protective compound is crosslinked to itself and to functional moieties derived from the medical apparatus.

8. A method as claimed in claim 7 wherein the functional moieties derived from the medical apparatus are from the material from which the apparatus is made.

9. A method as claimed in claim 7 wherein the functional moieties derived from the medical apparatus are from a primer layer.

10. A method as claimed in claim 1 wherein in the applying step, the protective compound is dispersed in an aqueous solution.

11. A method as claimed in claim 10 wherein the aqueous solution of the protective compound has a solids content from about 2% to about 80% by weight.

12. A method as claimed in claim 11 wherein the solids content is from about 10 to about 50 weight percent.

13. A method as claimed in claims 1 or 10 wherein in the applying step, the protective compound is a urethane.

14. A method as claimed in claims 1 or 10 wherein in the applying step, the protective compound is an acrylic.

15. A method as claimed in claim 13 wherein the urethane is dispersed in an aqueous solution containing triethylamine and N methyl 2 pyrrolidone.

16. A method as claimed in claim 1 wherein the slip additive in the applying step is hydrophobic.

17. A method as claimed in claim 1 wherein the slip additive in the applying step is hydrophilic.

18. A method as claimed in claim 1 wherein the slip additive is a silicon containing compound.

19. A method as claimed in claim 18 wherein the slip additive is a silicone.

20. A method as claimed in claim 18 wherein the slip additive is a siloxane.

21. A method as claimed in claim 20 wherein the siloxane is dimethyl siloxane.

22. A method as claimed in claim 17 wherein the slip additive is a polyvinyl pyrrolidone copolymer.

23. A method as claimed in claim 1 wherein the slip additive in the applying step is in the form of an emulsion.

24. A method as claimed in claim 23 wherein the coating solution in the applying step further comprises a pigment.

25. A method as claimed in claim 23 wherein the coating solution in the applying step further comprises a radioopaque compound.

26. A method as claimed in claim 23 wherein the coating solution in the applying step further comprises a therapeutic agent.

27. A method as claimed in claim 23 wherein the coating solution in the applying step further comprises an antimicrobial agent.

28. A method as claimed in claim 1 wherein the surface of the medical apparatus in the applying step is made of a material having moieties capable of crosslinking with the protective compound.

29. A method as claimed in claim 28 wherein the moieties capable of crosslinking are carboxyl moieties.

30. A method as claimed in claim 1 wherein the surface of the medical apparatus in the applying step is made of polyethylene terephthalate.

31. A method as claimed in claim 1 wherein the surface of the medical apparatus in the applying step is coated with a primer.

32. A method as claimed in claim 31 wherein the primer has functional moieties capable of crosslinking with the protective compound.

33. A method as claimed in claim 32 wherein the functional moieties are carboxyl moieties.

34. A method as claimed in claim 31 wherein the primer comprises ethylene acrylic acid.

35. A method as claimed in claim 1 wherein the medical apparatus in the applying step comprises a balloon.

36. A method as claimed in claim 1 wherein the medical apparatus in the applying step comprises a catheter.

37. A method as claimed in claim 1 wherein the medical apparatus in the applying step comprises a guidewire.

38. A method for providing a protective, lubricious coating on a surface of a medical apparatus, the method comprising:
applying a coating solution to a surface of the medical apparatus such that a protective, lubricious layer comprising a binder of a protective, lubricious layer comprising a binder of a protective compound containing domains of a slip additive is formed upon the apparatus surface,
wherein the coating solution comprises the protective compound and lubricating amounts of the slip additive and the formed layer contains the protective compound being cross-linked to both itself and to functional moieties derived from the medical apparatus.

39. A method as claimed in claim 38 wherein the coating solution in the applying step further comprises a crosslinking agent for the protective compound.

40. A method as claimed in claim 39 wherein the crosslinking agent enhances the adhesion of the coating to the medical apparatus.

41. A method as claimed in claim 39 wherein the crosslinking agent is aziridine.

42. A method as claimed in claim 39 wherein the crosslinking agent is carbodiimide.

43. A method as claimed in claim 38 wherein the functional moieties derived from the medical apparatus are from the material from which the apparatus is made.

44. A method as claimed in claim 38 wherein the functional moieties derived from the medical apparatus are from a primer layer.

45. A method as claimed in claim 38 wherein in the applying step, the protective compound is dispersed in an aqueous solution.

46. A method as claimed in claim 38 wherein in the applying step, the protective compound is a urethane.

47. A method as claimed in claim 38 wherein the slip additive in the applying step is hydrophobic.

48. A method as claimed in claim 38 wherein the slip additive in the applying step is hydrophilic.

49. A method for providing a protective, lubricious coating on surfaces of medical apparatus, the method comprising:
applying a coating solution comprising a protective compound and a silicon containing compound to a surface of the medical apparatus; and
forming a protective, lubricious layer upon the apparatus surface containing the protective compound and lubricating amounts of the silicon containing compound, the formed layer comprising the protective compound as a binder to maintain domains of the slip additive.

50. A medical apparatus having a protective, lubricious surface coating, the coating comprising a binder formed of the protective compound and lubricating amounts of a slip additive such that the binder maintains domains of the slip additive.

51. An apparatus as claimed in claim 50 wherein the coating further comprises a crosslinking agent.

52. An apparatus as claimed in claim 51 wherein the crosslinking agent is aziridine.

53. An apparatus as claimed in claim 51 wherein the crosslinking agent is carbodiimide.

54. An apparatus as claimed in claim 50 wherein the protective compound is a urethane.

55. An apparatus as claimed in claim 50 wherein the slip additive is hydrophobic.

56. An apparatus as claimed in claim 50 wherein the slip additive is hydrophilic.

57. An apparatus as claimed in claim 50 wherein the slip additive is a silicone or siloxane.

58. An apparatus as claimed in claim 57 wherein the slip additive is dimethyl siloxane.

59. An apparatus as claimed in claim 50 wherein the surface upon which the coating is applied comprises polyethylene terephthalate.

60. An apparatus as claimed in claim 50 which comprises a balloon.

61. An apparatus as claimed in claim 50 which comprises a catheter.

62. An apparatus as claimed in claim 50 which comprises a guidewire.

63. An apparatus as claimed in claim 50 having a primer layer disposed between the coating and surface.

64. An apparatus as claimed in claim 63 wherein the primer layer has a functionality suitable for crosslinking with the coating.

65. An apparatus as claimed in claim 64 wherein the functionality is a carboxyl functionality.

66. An apparatus as claimed in claim 63 wherein the primer layer comprises ethylene acrylic acid.

67. An apparatus as claimed in claim 50 wherein the slip additive is hydrophilic and can be bound to both the protective compound and a functionality group derived from the medical apparatus.

68. An apparatus as claimed in claim 50 wherein the coating further comprises a pigment.

69. An apparatus as claimed in claim 50 wherein the coating further comprises a radioopaque compound.

70. An apparatus as claimed in claim 50 wherein the coating further comprises a therapeutic agent.

71. An apparatus as claimed in claim 50 wherein the coating further comprises an antimicrobial agent.

72. A medical apparatus having a protective, lubricious surface coating, the coating comprising a protective compound and a slip additive, the protective compound being crosslinked to moieties derived from the medical apparatus thereby strengthening the overall coating.

73. A medical apparatus having a protective, lubricious surface coating, the coating comprising a binder formed of a protective compound to maintain domains of lubricating amounts of a silicon containing compound for enhancing the lubricity of the coating.

* * * * *